United States Patent [19]

Tien

[11] Patent Number: 5,662,105
[45] Date of Patent: Sep. 2, 1997

[54] SYSTEM AND METHOD FOR THE EXTRACTMENT OF PHYSIOLOGICAL SIGNALS

[75] Inventor: Jonathan Tien, Redmond, Wash.

[73] Assignee: SpaceLabs Medical, Inc., Redmond, Wash.

[21] Appl. No.: 442,834

[22] Filed: May 17, 1995

[51] Int. Cl.$^6$ ............................................. A61B 5/00
[52] U.S. Cl. ............................................. 128/633
[58] Field of Search ........................... 128/633, 664, 128/665; 356/41; 364/413.01, 413.02, 413.03

[56] References Cited

U.S. PATENT DOCUMENTS

| | | | |
|---|---|---|---|
| 4,458,691 | 7/1984 | Netravali | 128/705 |
| 4,537,200 | 8/1985 | Widrow | 128/696 |
| 4,649,505 | 3/1987 | Zinser, Jr. et al. | 379/411 |
| 4,799,493 | 1/1989 | DuFault | 128/705 |
| 4,955,379 | 9/1990 | Hall | 128/633 |
| 4,956,867 | 9/1990 | Zurek et al. | 381/94.1 |
| 5,188,108 | 2/1993 | Secker | 128/633 |
| 5,482,036 | 1/1996 | Diab et al. | 128/633 |

FOREIGN PATENT DOCUMENTS

| | | |
|---|---|---|
| 0 303 502 | 2/1989 | European Pat. Off. . |
| WO92/15955 | 9/1992 | WIPO ............ G06F 15/42 |

Primary Examiner—Lee S. Cohen
Assistant Examiner—Eric F. Winakur
Attorney, Agent, or Firm—Seed and Berry LLP

[57] ABSTRACT

A technique for the accurate determination of artifact free pulse oximetry signals utilizes an adaptive signal processor and peak detector circuit. A reference signal for the adaptive signal processor is derived based on mathematical relations of the detected light signals and the true intensity of light signals. The derivation of the appropriate reference signal requires the determination of peak values for two ratio constants. The two ratio constants lie within a known physiological range of values. When the value of the ratio constants has been determined, the reference signal equals the true intensity. The output of the adaptive signal processor is provided to the peak detector. The peak detector subdivides the known physiological range into two intervals and determines in which interval a peak exists. The remaining interval is discarded, and the peak detector repeats the measurement on the remaining interval until a peak has been detected within the desired accuracy. The value corresponding to the detected peak is one of the ratio constants. In a second alternative embodiment, the output of the adaptive filter is fed directly to the peak detector to determine values for the two ratio constants. In yet a third embodiment, two adaptive signal processors are coupled to a ratio processor. The output of the ratio processor is at a minimum when the appropriate value is selected for each of the two ratio constants.

20 Claims, 8 Drawing Sheets

SYSTEM AND METHOD FOR THE EXTRACTMENT OF PHYSIOLOGICAL SIGNALS

TECHNICAL FIELD

The present invention relates generally to signal processing and, more particularly, to a system and method for processing physiological signals in the presence of noise to extract the physiological signals.

BACKGROUND OF THE INVENTION

The measurement of physiological signals is difficult because the underlying physiological processes generate very low level signals and interfering noise is inherent in the body and the interface between the body and sensors of the physiological processes. For example, measurement of electrocardiogram (ECG) signals are based on the electrical activity generated by the electrical depolarization of the heart muscle. The signals are typically detected by surface electrodes mounted on the chest of the patient. The signals are initially weak at the signal source (i.e., the heart) and are even weaker at the surface of the chest. Furthermore, electrical interference from the activity of other muscles, noise caused by patient breathing, general movement, and the like cause additional interference with the ECG signal. External electrical interference, such as 60 Hertz (Hz) interference also compounds the ECG measurement problem. Therefore, great care must be taken in the design and use of physiological processors to enhance the quality of the desired signal and reduce the effects of interfering signals.

Another common physiological measurement that is made difficult by the presence of interfering noise is the measure of oxygen saturation in the blood. This measurement is frequently performed with a pulse oximeter 1, illustrated in the functional block diagram of FIG. 1. A transmissive pulse oximetry sensor 2 is placed on a finger 4 of the patient. First and second light sources 6 and 8 are directed through the fleshy portion of the finger 4 and detected by one or more light detectors 10 on the opposite side of the finger. As is well known in the art, the light from light sources 6 and 8 are of different wavelengths that are differentially absorbed by oxygenated blood cells. The first light source 6 is typically designated as a Red light source having a wavelength in the red region of the spectrum. The second light source 8 is typically designated the IR source having a wavelength in the near infrared region of the spectrum.

The pulse oximeter 1 determines the oxygen saturation based on a ratio of the light detected from the Red light source 6 and the IR light source 8, respectively. A ratio calculator 12 determines the ratio of detected light and uses the value of the ratio as an address in a look-up table 14. The look-up table 14 contains data relating the ratio of detected light to the oxygen saturation in the blood. A typical oxygen saturation curve 18 is illustrated in FIG. 2 where the percentage of oxygen saturation is plotted against the ratio of detected light from the Red light source 6 and the IR light source 8 (see FIG. 1). Pulse oximeters may also use reflective pulse oximetry sensors (not shown) in which the light sources and light detectors are positioned adjacent each other, and the light from the light sources is reflected back to the detector(s) by oxygenated blood cells in the finger 4.

The measurement of blood oxygen saturation is important for physicians that are monitoring a patient during surgery and at other times. As with other physiological measurements, pulse oximetry measurement also is susceptible to interference form noise. As is known in the art, pulse oximetry is particularly susceptible to interference from stray light and from patient motion. Stray light detected by the light detector 10 can cause erroneous calculation of the ratio. Known techniques are employed to reduce the interference caused by stray light. The interference from patient motion is a much more difficult noise source and is the subject of intensive research.

Therefore, it can be appreciated that there is a significant need for a system and method for measurement of physiological signals that enhances the desired signal in the presence of interfering noise signals. This and other advantages provided by the present invention are described in the detailed description and accompanying figures.

SUMMARY OF THE INVENTION

The present invention is embodied in a system and method for the enhancement of signals in the presence of noise. The system includes a detector to detect first and second signals, each of the detected signals having a signal portion and an interference portion. The system includes an adaptive signal processor having a signal input, an adaptive filter input, an adaptive filter output, and an error signal output wherein the error signal output is coupled to the adaptive filter to adjust the adaptive filter such that the error signal has minimum correlation with the filter input. The signal input of the adaptive filter is coupled to the detector to receive the first detected signal. A peak detector receives a signal from the adaptive signal processor and determines a ratio constant corresponding to a peak value of the signal from the adaptive signal processor over a predetermined range of possible ratios. A storage location contains a mathematical relationship of the first and second portions of the first and second detected signals and a ratio constant. A reference signal generator coupled to the peak detector and to the storage location generates the signal portion of the first detected signal based on the mathematical relationship and the ratio constant. The signal portion of the first detected signal may be coupled to the filter input to permit the adaptive filter to generate a filtered version of the first portion of the first detected signal. The signal from the adaptive signal processor and received by the peak detector may be the error signal output or the adaptive filter output.

In one embodiment, the peak detector subdivides the predetermined range into first and second substantially equal ranges and determines peak location in either the first or second ranges. The peak detector continues to subdivide the range containing the peak until the peak detector determines the first ratio constant corresponding to the peak location. This technique advantageously permits the peak detector to quickly locate a peak without the necessity of scanning the entire range of ratio values.

In another embodiment, the reference signal generator uses the mathematical relationship and the first ratio constant to generate the signal portion of the second detected signal. The signal portion of the second detected signal may be applied to the filter input as a second reference signal. This permits the adaptive filter to generate a filtered version of the first portion of the second detected signal.

In yet another alternative embodiment, signal inputs of first and second adaptive signal processors receive the first and second detected signals, respectively. First and second reference signals are generated and coupled to the adaptive filter inputs of the first and second adaptive signal processors, respectively. The filter outputs of the first and second adaptive filters are coupled to a ratio processor, which generates a ratio output indicative of the difference between ratio constants in the first and second reference signals, and desired values of the ratio constants. The ratio output is at a minimum when the selected ratio constants in the first and second reference signals are equal to the desired ratio constants.

In one application, the system is used to extract physiological signals for the measurement of blood oxygen in a subject. The system includes first and second light sources to direct light of different wave length toward the subject. A light detector is positioned to detect the first and second lights after passage through the subject, with each of the detected light signals having first and second portions. The light detector generates signals indicative of an intensity of the first and second detected light signals. The first portion of the detected light signal arises from the light transmitted from the light source, and the second portion of the detected signal arises from interference source. In this embodiment, the adaptive signal processor has a signal input coupled to the light detector and the reference input coupled to a reference signal generator. The reference signal generator uses the mathematical relationship of the first and second detected signals and ratio constants to generate the reference signal. A peak detector is used to determine correct values of the first and second ratio constants, such that the reference signal is indicative of the first portion of the detected signal, and the output of the adaptive filter is a wave form representing the true intensity of light transmitted through the subject.

DETAILED DESCRIPTION OF THE INVENTION

Figure 1:
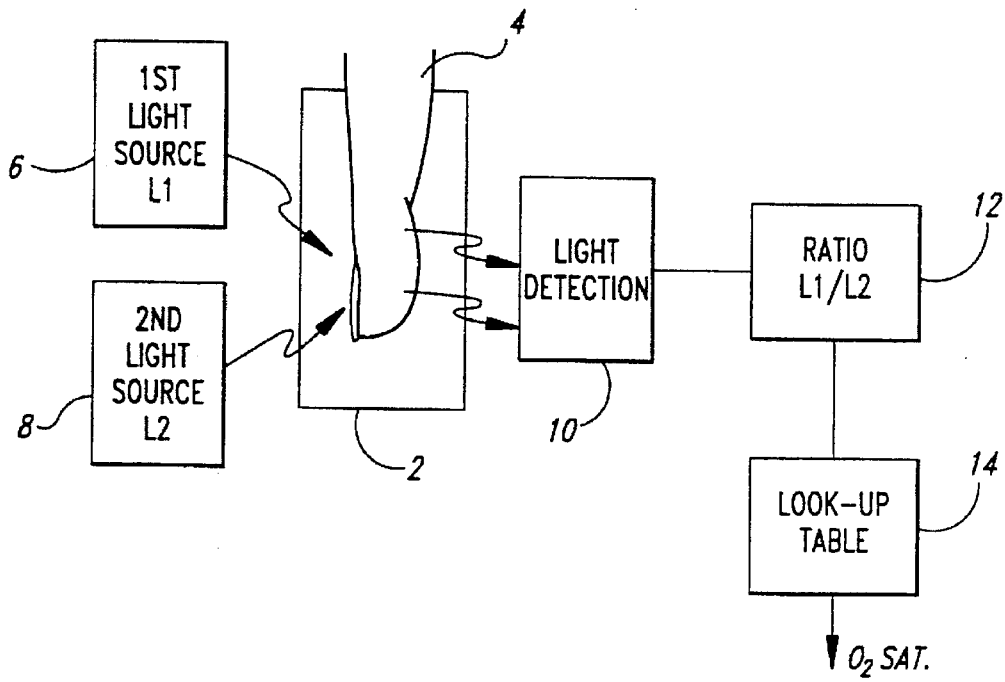
FIG. 1 is a functional block diagram of a prior art oximetry system.

Measurement of physiological signals in the presence of interference is a difficult task, particularly if the interference is somewhat random rather than periodic. A number of different techniques can potentially be used to separate the desired physiological signal from the interfering noise signal. For example, a filter can sometimes be used to remove the interfering noise signal. Notch filters, such as a 60 Hz notch filter, can be used to minimize interference from line noise. Similarly, high frequency interference noise signals can be eliminated with a lowpass filter designed to pass the physiological signal of interest and to reject frequencies above the physiological signal bandwidth. However, some interference sources have the same or similar frequency content as the physiological signal of interest. For interference of this type, different signal processing technologies must be employed.

Adaptive signal processing is one well known technique for the separation of a desired signal from an interference signal. Adaptive signal processing is based on the assumption that the noise caused by the interference signal is uncorrelated to the desired signal. A conventional adaptive signal processor, configured as a correlation canceller, is illustrated in the functional block diagram of FIG. 3. An adaptive processor 20 has a signal input 22 and a reference input 24. The reference input 24 is fed to an adaptive filter 28. The adaptive filter 28 generates a filter output 30 that is subtracted from the signal input 22 in a conventional subtractor 34. The subtractor 34 generates an error signal 38 that is fed back to the adaptive filter 28. The error signal 38 has a value designated herein as $\epsilon$. The adaptive filter 28 is automatically adjusted so that the error signal 38 has a minimum correlation with the reference input 24. Thus, the adaptive filter 28 is adjusted so that the subtractor 34 cancels any correlated signal in the signal input 22. The error signal 38 is the system output and contains the portion of the input signal 22 that is uncorrelated to the reference input 24. In a typical application of adaptive filtering, the signal input 22 consists of a combination of a pure input signal from a device, such as a sensor, and a noise signal from one or more sources. The reference input 24 should then be a signal that is related to and at least partially correlated with, the noise signal. The adaptive filter 28 is adjusted so that the error signal 38 is the pure input signal since the pure input signal has a minimum correlation with the reference signal applied to the reference input 24.

Adaptive signal processing has been successfully applied to the measurement of physiological signals when the source of the interference signal is well characterized. For example, the physician may wish to listen to a fetal heartbeat whose acoustical signal strength is relatively small compared to the acoustical strength of the mother's heartbeat. As discussed above, simple filtering will not work satisfactorily because the two heartbeats have similar frequency content. However, adaptive signal processing can isolate the fetal heartbeat by using the much louder maternal heartbeat as the reference input 24 and the combination of fetal and mammal heartbeats as the signal input 22. Because the two heartbeats are uncorrelated and the maternal heartbeat can be independently derived, the adaptive signal processor 20 can easily isolate the fetal heartbeat. Similarly, the adaptive signal processor 20 can remove 60 Hz interference by simply using the 60 Hz signal as the reference input 24. Thus, adaptive signal processing can effectively remove the undesirable interference signal provided that the interference signal can be independently derived.

However, some physiological signals of interest do not have an independent interference source to use as the reference input 24. For example, pulse oximetry is susceptible to motion artifact, as described above. The motion alters the path that the light takes through the finger 4 (see FIG. 1) and the characteristics of the interface between the finger 4 and the sensor 2. As the light from the Red light source 6 and the IR light source 8 pass through the fleshy portion of the finger 4, each is contaminated by a noise signal, primarily due to patient motion. The detected light is thus the combination of the true light transmitted through the finger 4 plus the interfering noise introduced in the measurement process. This may be illustrated by the following equations:

$$R = R^* + N \quad (1)$$

$$r = r^* + n \quad (2)$$

where R is the light intensity measured by the light detector 10 (see FIG. 1), R* is the true intensity of light transmitted by the Red light source 6, and N is the noise source introduced by the measurement process while measuring the intensity of the Red light. Similarly, r in equation (2) is the light intensity measured by the light detector 10, r* is the true intensity of light transmitted by the IR light source 8, and n is the noise source introduced by the measurement process while measuring the intensity of the IR light.

The goal of the measurement process is to determine the ratio of the true intensity of Red light, R*, transmitted through the finger 4 to true intensity of IR light, r*, transmitted through the finger. However, most pulse oximetry system determine the ratio of the measured signal (i.e., R/r) or some processed version of the measured intensities due to an inability to determine the true intensity. The ratio of intensities, whether it is the ratio of measured intensities, true intensities, or some processed version of the measured intensities, is designated herein as $r_a$.

Some prior art pulse oximetry systems attempt to minimize the effects of motion artifact through conventional filtering or modulation of the intensity of the light sources 6 and 8. However, these processing techniques are not particularly effective because the motion artifact is caused primarily by movement of venous blood in the tissues of the finger 4 rather than from some external noise source such as stray light. Conventional filtering may remove some undesirable noise, but the frequency content of the motion artifact is similar to that of the desired signal. Modulation techniques may reduce interference from stray ambient light, but have little effect on motion artifact because the primary noise source (e.g., venous blood movement resulting from patient motion) originates in the measurement pathway. Thus, the ratio determined by many pulse oximetry systems is not accurate.

It should be noted that the intensity of detected light varies with the patient's heart beat thus creating a time-varying pulsatile waveform. The pulsatile waveform contains an alternating current (AC) signal component and a direct current (DC) component. A more accurate determination of the ratio $r_a$ is given by the following equation:

$$r_a = \frac{(Red_{AC}/Red_{DC})}{(IR_{AC}/IR_{DC})} \quad (3)$$

where $Red_{AC}$ is the AC component of the intensity of the measured Red light, R, $Red_{DC}$ is the DC component of the intensity of the measured Red light, $IR_{AC}$ is the AC component of the intensity of the measured IR light, r, and $IR_{DC}$ is the DC component of the intensity of the measured IR light. In practice, the DC components tend to cancel each other out thus normalizing the resultant ratio of AC components. Thus equations (1) and (2) above may be more accurately shown as:

$$R(t) = R^*(t) + N(t) \quad (4)$$

$$r(t) = r^*(t) + n(t) \quad (5)$$

where $R(t) = Red_{AC}$ and $r(t) = IR_{AC}$ to reflect the time varying nature of the signals.

Figure 4:
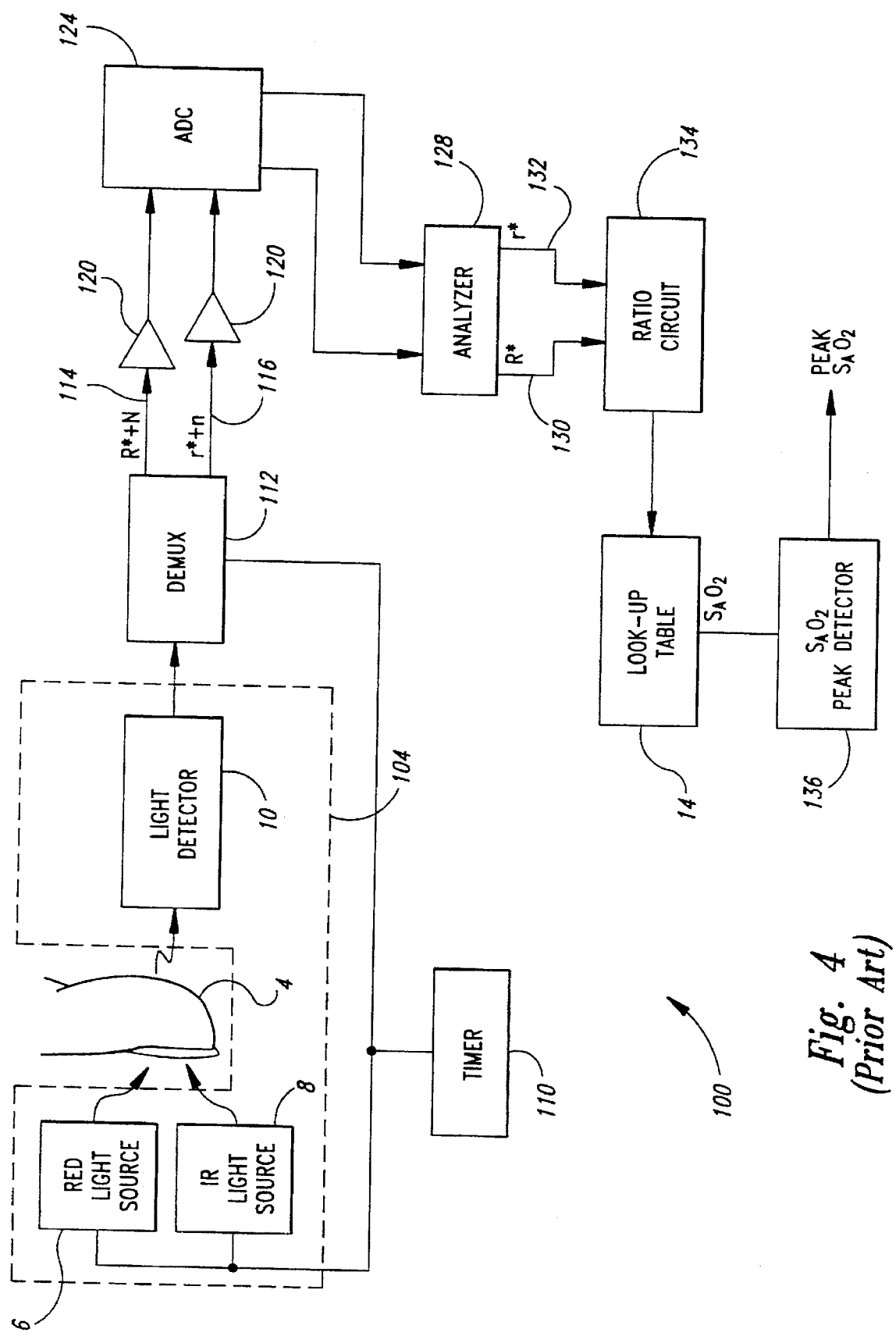
FIG. 4 is a detailed functional block diagram of the system of FIG. 1.
Figure 5:
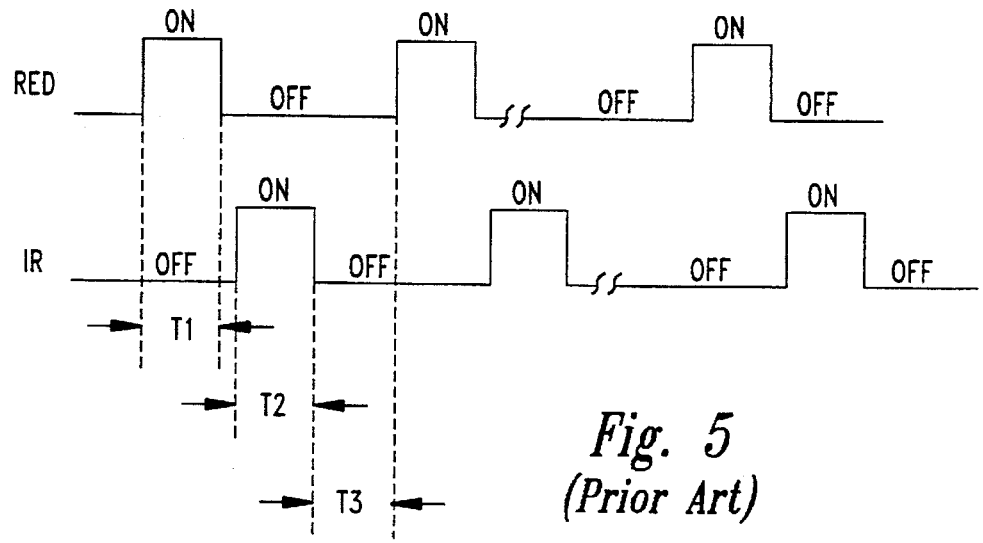
FIG. 5 are waveforms that illustrate the timing control of light sources used by the system of FIG. 4.

A typical prior art transmissive pulse oximetry system 100 is illustrated in the functional block diagram of FIG. 4, where the sensor 2 contains the Red light source 6 and the IR light source 8, typically on the same side of the patient's finger 4. The Red and IR light sources 6 and 8 are alternately activated by a timer 110. The activation timing of the first and second light sources 6 and 8 is illustrated in the waveform of FIG. 5. The Red light source 6 is activated in the period T1. Following the period T1, the IR light source 8 is activated during the period T2. Following the period T2, neither the Red light source 6 or the IR light source 8 is activated during the period T3. The pulse oximeter uses the period T3 to detect stray ambient light and determine a baseline value to compensate for the stray ambient light. Compensation of stray light is well known by those of ordinary skill in the art and will not be discussed herein. The timer 110 repeats the pulsation of the Red light source 6 and the IR light source 8 in the manner described above. It should be noted that the intensity of the light from the Red light source 6 and the IR light source 8 is automatically adjusted by a closed-loop system to assure an acceptable detected signal level. This closed-loop gain control is well known in the art and need not be discussed herein.

The detector 10 detects light transmitted through the fleshy portion of the finger 4. The signals generated by the light detector 10 are passed to a demultiplexor 112. The demultiplexor 12 is coupled to the timer 110 and is controlled by the timer 110 to generate an independent signal for the light detected from each of the light sources 6 and 8, respectively. The time division multiplexing used by the system 100 is well understood and will not be discussed in detail herein. As discussed above, the timer 110 enables the Red light source 6 during the period T1. During that same period T1, the timer also controls the demultiplexor 112 so that the detected signals from the Red light source 6 are routed to a data line 114. During the time period T2, the timer 110 enables the IR light source 8 and controls the demultiplexor 112 so that the detected signals from the IR light source are routed to a data line 116. Each of the data lines 114 and 116 can be coupled to optional amplifiers 120. The amplified signals are coupled to the inputs of an analog to digital converter (ADC) 124 that digitizes the signal in a conventional manner. It should be noted that the amplifiers 120 may be integrally formed as part of the ADC 124. The ADC 124 may also include optional lowpass filters (not shown) to assure that the analog signals are bandlimited below the Nyquist rate of the ADC.

The demultiplexor 112 is shown as a separate component in FIG. 4 for the sake of clarity. Those skilled in the art will recognize that the demultiplexing function can also occur after the signal from the light detector 10 has been digitized. The present invention is intended to encompass all such conventional techniques for demultiplexing the signals from the light detector 10.

The ratio circuit 134 receives the digitized signals and uses the ratio of R(t)/r(t) to determine a location in the look-up table 14. Assuming that no motion artifact is present, the data entry in the look-up table 14 corresponds to the blood oxygen saturation. In reality, the ratio calculated by the ratio circuit 34 is inaccurate because of the motion artifact.

Figure 3:
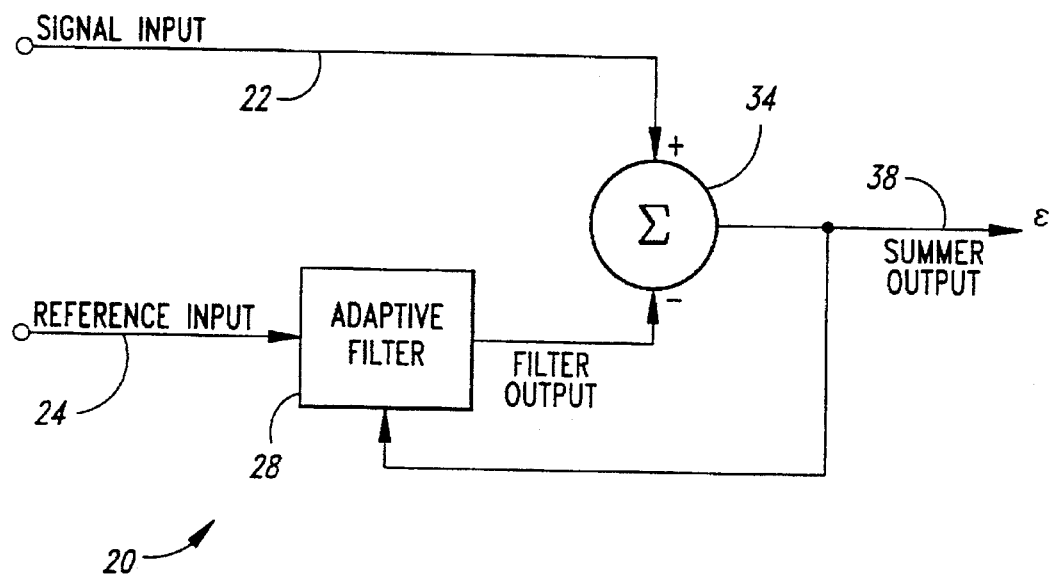
FIG. 3 is a functional block diagram of a conventional adaptive signal processor.

A technique has been developed to use the conventional adaptive signal processor of FIG. 3 to eliminate the motion artifact. A reference signal related to the motion artifact interference source is independently derived and applied as the reference input 24 to the adaptive signal processor 20. The reference input 24 uses detected signals from the Red and IR light sources 6 and 8. These techniques are described in PCT Patent Publication No. WO92/15955, published on Sep. 17, 1992. The system described in this publication generates a reference signal related to the interference noise and uses this noise reference in the correlation canceller version of the adaptive signal processor 20 shown in FIG. 3. The adaptive signal processor 20 uses the noise reference to cancel the noise in the measured signal thus resulting in a signal that is representative of the true signal (i.e., the measured signal minus the noise signal).

The noise reference signal generated by the prior art pulse oximeter has the following form:

$$N(t) = R(t) - \omega r(t) \quad (6)$$

where $N(t)$ is the time varying noise reference signal, $R(t)$ is the time varying detected signal from the Red light source 6 (i.e., true intensity plus noise), $r(t)$ is the time varying signal from the detected signal from the IR light source 8 (i.e., true intensity plus noise) and $\omega$ is a selected value of the ratio $r_a$. Equation (6) has been empirically derived to model the noise source.

Figure 2:
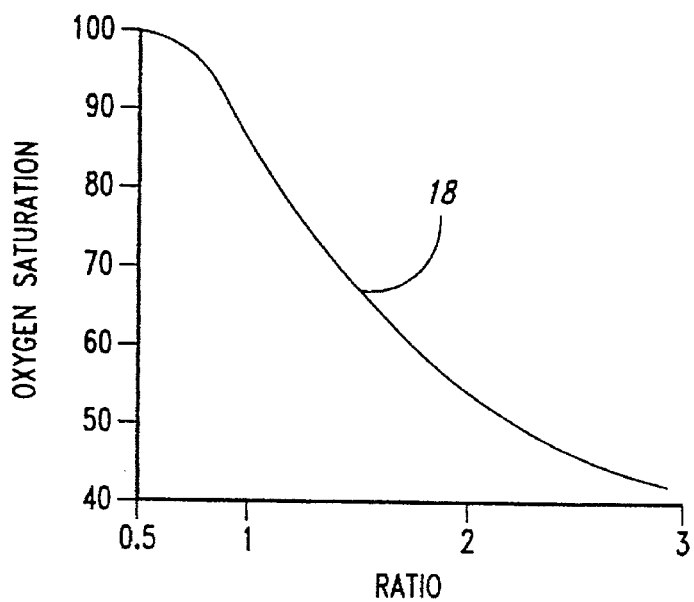
FIG. 2 is a typical oxygen saturation curve employed by the system of FIG. 1 to determine blood oxygen saturation.

As can be seen from Equation (6) above, the prior art pulse oximeter must determine a value for $\omega$ in order to generate the noise reference signal $N(t)$. As seen in FIG. 2, the ratio of the light intensities and thus the value of $\omega$ lies within a range from 0.5 to 3.0. The limitation in the range of values for $\omega$ is imposed by the physiology. That is, the oxygen saturation value lies between 100% and 0%, with the corresponding ratios lying between a value of 0.5 to 3.0, respectively. To compensate for variations in the sensitivity of the sensor 2, a range of ratio values from 0.3 to 3.0 is typically used. The prior art pulse oximeter takes advantage of the knowledge that the ratio must lie within the range from 0.3 to 3.0 and scans the entire range of possible values for the ratio and inserts each of these values into equation (6) above. The noise reference signal for each possible value of the ratio $r_a$ is provided as the reference input 24 (see FIG. 3) to the adaptive signal processor 20. The adaptive signal processor 20 in turn generates the value $\epsilon$ for each of the possible values of the ratio. A typical output of the value $\epsilon$ versus the ratio $r_a$ is illustrated by a waveform 48, shown in FIG. 6. The best estimate of the value of $\omega$ is given by a peak 50 or a peak 52 of the waveform 48. It is known that if the value of $\omega$ corresponds to the peak 50, then $N(t)$ in equation (6) equals $C_1 n(t)$ where $C_1$ is a constant and $n(t)$ is the noise source introduced by the measurement process while measuring the intensity of light from the IR source 8 (see FIG. 4). If the value of $\omega$ corresponds to the peak 52, it is known that $N(t)$ in equation (6) equals $C_2 r^*(t)$ where $C_2$ is a constant and $r^*(t)$ is the true intensity of light transmitted by the IR light source 8. The value of $\omega$ corresponding to the peak 50 is inserted into equation (6) above to generate a noise reference signal $N(t)$ as the reference input 24 (see FIG. 3) of the adaptive signal processor 20. The error signal 38 is the noise signal $n(t)$ if the value of $\omega$ corresponds to the peak 52. However, if the value of $\omega$ corresponds to the peak 50, the reference signal $N(t)$ corresponds to the noise signal $n(t)$. The correlation canceller adaptive signal processor 20 cancels out the constant $C_1$ as well as correlated signals between the signal input 22 and the reference input 24 such that the error signal 38 is the desired signal. The true output signals are provided to the ratio circuit 12 (see FIG. 4) and processed in the manner previously described.

The disadvantage of this approach is that generating the value $\epsilon$ for each of the possible values of the ratio $r_a$ is a computationally difficult and time consuming approach to adaptive filter in pulse oximetry. As those skilled in the art can appreciate, real-time calculation of blood oxygen saturation is important to the physician. This real-time constraint can only be met with the prior art approach using expensive and powerful digital signal processor hardware.

The present invention is directed to alternative techniques for producing a blood oxygen saturation measurement. These techniques provide a more efficient computational process that does not generate the noise reference required by the prior art approach. Rather the present invention directly generates the desired signal (i.e., the true intensity) and does not use correlation cancellation techniques in the adaptive signal processor.

Figure 7:
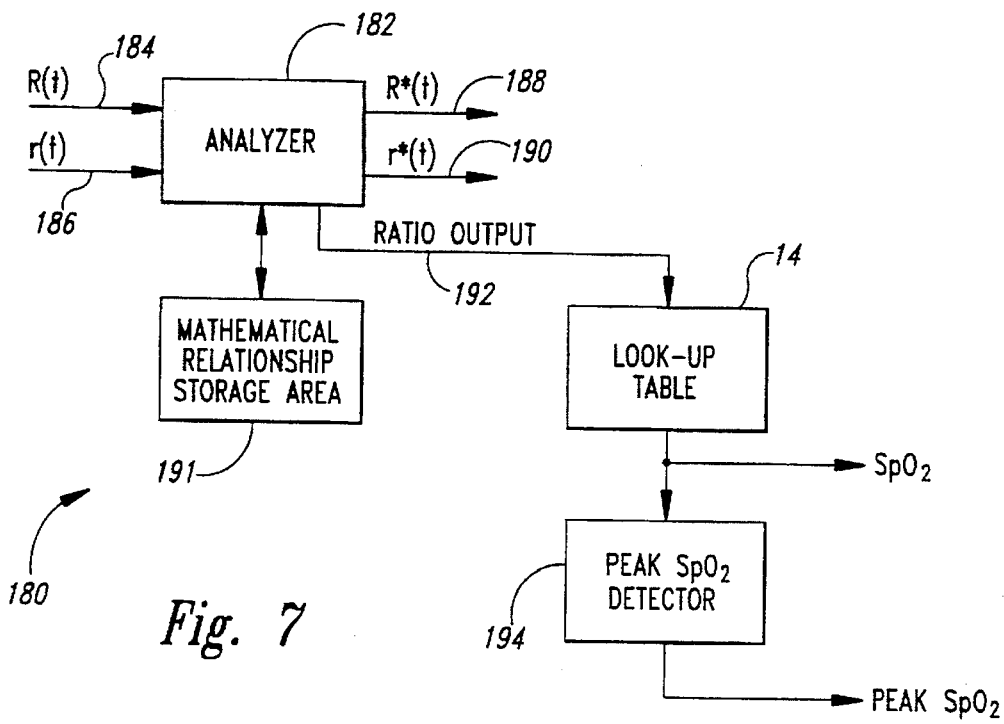
FIG. 7 is a functional block diagram of the present invention used with the system of FIG. 4.

The present invention is embodied in a system 180, shown in the functional block diagram of FIG. 7. An analyzer 182 coupled to the ADC 124 (see FIG. 4) receives digitized signals 184 representing the measured light intensity, $R(t)$, from the Red light source 6, and digitized signals 186 representing the measured light intensity, $r(t)$, from the IR light source 8. The analyzer 182 processes these signals using mathematical relationships between the measured signals and the true intensities, to generate a true intensity output 188 equal to the true intensity, $R^*(t)$, and a true intensity output 190 equal to the true intensity, $r^*(t)$. The mathematical relationships are stored in a mathematical relationship storage area 191 for use by the analyzer 182.

The analyzer 182 generates the ratio $r_a$ of true intensities (i.e., $R^*(t)/r^*(t)$) in the process of generating the true intensity outputs 188 and 190. A ratio output 192 is coupled to the lookup table 14 to permit the determination of oxygen saturation in a conventional manner. The output of the lookup table 14 is a value $S_pO_2$ corresponding to the blood oxygen saturation. The system 180 may also include an optional $S_pO_2$ peak detector 194 to generate signals indicative of the peak oxygen saturation. The true intensity outputs 188 and 190 are useful for monitoring the patient oximetry waveforms and for calculating continuous blood pressure measurements. Techniques for calculating blood pressure from pulse oximetry output waveforms are described in U.S. Pat. No. 5,269,310. The advantage of the present invention is that the desired signal is directly generated rather than the noise reference signal. Furthermore, the processing techniques of the present invention require far fewer computational steps thus improving the rate at which accurate data can be obtained.

Figure 6:
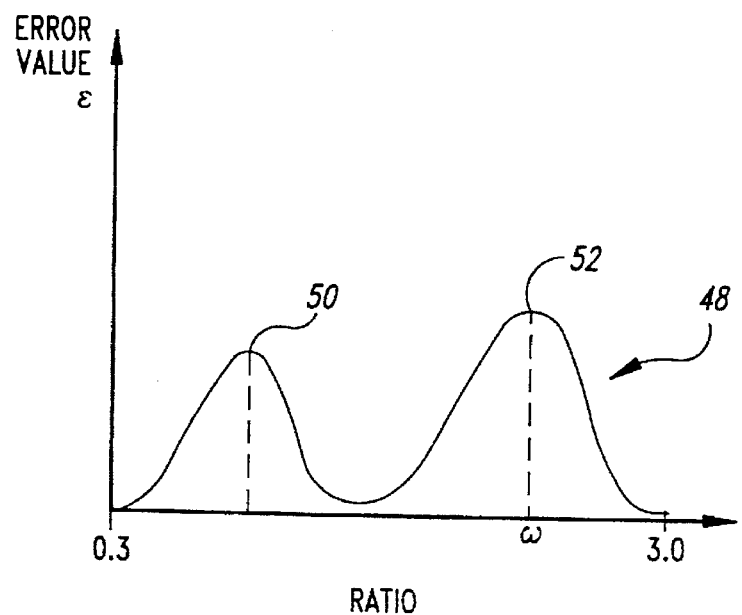
FIG. 6 illustrates a waveform used in the calculation of a reference noise signal by the conventional adaptive signal processor of FIG. 3.

With respect to FIG. 6, research has shown that the peak 50 corresponds to the ratio of the true intensities (i.e., $R^*(t)/r^*(t)$), while the peak 52 corresponds to the ratio of noise intensities (i.e., $N(t)/n(t)$). The following description provides details of the mathematical derivation of the reference signals representing the true intensities. For purposes of the following description, the ratio of the true intensities may be defined by the following equation:

$$\alpha = \frac{R^*(t)}{r^*(t)} \quad (7)$$

where $\alpha$ is the value of the ratio $r_a$ corresponding to the peak 50 (see FIG. 6), $R^*(t)$ is the time varying true intensity of light transmitted from the Red light source 6 and $r^*(t)$ is the time varying true intensity of light transmitted from the IR light source 8. The ratio of noise signals introduced by the measurement process is defined by the equation:

$$\beta = \frac{N(t)}{n(t)} \quad (8)$$

where $\beta$ is the value of the ratio $r_a$ corresponding to the peak 52 (see FIG. 6), $N(t)$ is the noise introduced during the measurement of the light transmitted by the Red light source 6 and n(t) is the noise introduced during the measurement of the light transmitted by the IR light source 8. It is also known that the following constraint exists between α and β:

$$0.3 < \alpha < \beta < 3.0 \tag{9}$$

because of the physiological nature of the signals. It is noted that the percentage of oxygen saturation is also a time-varying signal, changing by approximately 0.5% over time. However, it is assumed that the blood oxygen saturation is constant over the short period required to perform the measurements. Thus, α and β can be considered ratio constants for purposes of the present discussion.

Given equations (4)–(5) and (7)–(8), it is possible to express the relationship between α and β using the following matrix equation:

$$\begin{bmatrix} 1 & 0 & 1 & 0 \\ 0 & 1 & 0 & 1 \\ 1 & -\alpha & 0 & 0 \\ 0 & 0 & 1 & -\beta \end{bmatrix} \times \begin{bmatrix} R^*(t) \\ r^*(t) \\ N(t) \\ n(t) \end{bmatrix} = \begin{bmatrix} R(t) \\ r(t) \\ 0 \\ 0 \end{bmatrix} \tag{10}$$

where it is assumed that $\alpha \neq \beta$. As previously stated, it is known that the primary cause of noise in transmissive pulse oximetry measurements is motion artifact caused by the movement of venous blood in the finger 4. Thus, the value β in equation (8) is related to oxygen saturation in the venous blood. The assumption that $\alpha \neq \beta$ is based on the understanding that α is a measure of arterial blood oxygenation while β is related to venous blood oxygenation. As the body takes oxygen from the blood, blood oxygenation decreases as blood moves from the arterial portion of the circulation system to the venous portion of the circulation system. Thus, the measure of arterial oxygenation, measured by α, is not the same as β, which is related to venous oxygenation.

The significance of equation (10) is that all signal components can be explicitly calculated as a function of the input signals and the ratio constants α and β. The true signal components, R*(t) and r*(t) can also be explicitly derived using equation (10) above. The true signal components, R*(t) and r*(t), can be expressed by the following equations, which are derived from equation (10):

$$R^*(t) = \frac{\alpha R(t) - \alpha \beta r(t)}{\alpha - \beta} \tag{11}$$

$$r^*(t) = \frac{R(t) - \beta r(t)}{\alpha - \beta} \tag{12}$$

It will be noted that the above equations (11) and (12) provide the true signal components, R*(t) and r*(t) as a function of the measured signals, R(t) and r(t), available from the sensor 2 (see FIG. 4) and the ratio constants α and β. The values of the ratio constants α and β are not known and must be determined by the system 180. The following description details a number of alternative techniques for deriving the value of the ratio constants α and β.

Various embodiments of the analyzer 182 are described below. The analyzer 182 does not require a noise reference signal generated by the measured signals as does the prior art oximeter. Rather, the analyzer 182 directly derives a true intensity output 188 corresponding to the true intensity R* of light transmitted through the finger 4 from the Red light source 6 (see FIG. 4) and a true intensity output 132 corresponding to the true intensity r* of light transmitted through the finger from the IR light source 8. The system 180 uses the ratio of R*(t)/r*(t) (i.e., α) and the waveform of FIG. 2 to determine the blood oxygen saturation in a conventional manner.

Figure 8:
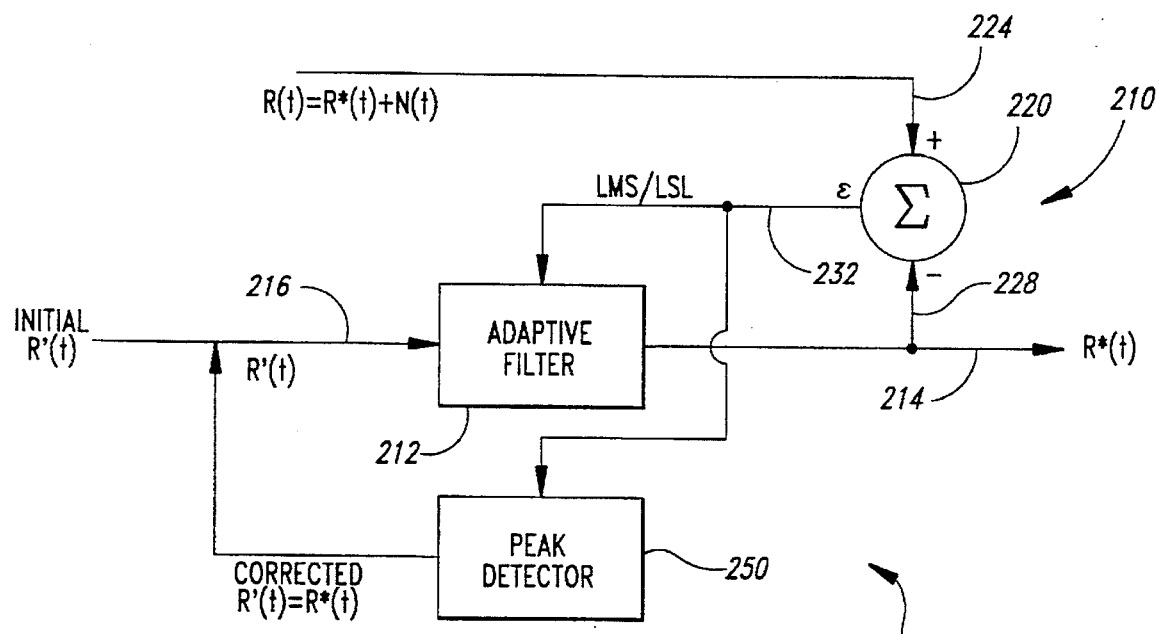
FIG. 8 illustrates a first embodiment of the system of FIG. 7.

A first embodiment of the analyzer 182, shown in the functional block diagram of FIG. 8, uses an adaptive signal processor 210. Although similar to the adaptive signal processor 20 of FIG. 3, the adaptive signal processor 210 does not use correlation cancellation techniques with a noise reference signal. Rather, the adaptive signal processor has an adaptive filter 212 with a filter output 214 that directly generates the desired output signal R*(t) if the appropriate signal is selected for a reference input 216 to the adaptive filter.

A subtractor 220 has a positive subtractor input 224 and a negative subtractor input 228. The measured signal R(t), which is the combination of the true signal, R*(t), and the noise signal, N(t), is coupled to the positive subtractor input 224, while the filter output 214 is coupled to a negative subtractor input 228. The subtractor 220 generates an error signal 232 that is fed back to the adaptive filter in a well known manner. The adaptive signal processor 210 uses an iterative process to adjust the adaptive filter 212 to minimize the error signal 232. Minimization techniques, such as least mean squares (LMS) or least squares lattice (LSL), are used to adjust the adaptive filter 212. These techniques are well known in the art of adaptive signal processing and need not be discussed herein.

The reference input 216 is provided with a signal R'(t) derived from equation (11) to estimate the true intensity R*(t). The signal R'(t) is simply the signal of equation (11) for selected values of the ratio $r_a$ over the range from 0.3 to 3.0 to determine values for the ratio $r_a$ corresponding to the peaks 50 and 52, respectively. The analyzer 182 does not scan the entire range from 0.3 to 3.0 as does the prior art pulse oximeter. In contrast, only selected values for the ratio $r_a$ between 0.3 and 3.0 are used to determine the correct values of the ratio constants α and β thus resulting in a more computationally efficient approach to pulse oximetry. Furthermore, the prior art reference signal of equation (6) must be used as a reference signal in the correlation cancellation adaptive signal processor 20 of FIG. 3, so that the error signal 38 is the desired signal. In contrast, the analyzer 182 of the present invention directly generates the desired signals using the mathematical relations of equation 10. When the correct values for the ratio constants α and β have been determined, the function R'(t)=R*(t). Again, it should be noted that the signal generated by the analyzer 182 is mathematically derived and equals the desired true intensity if the correct values are selected for α and β. This approach is markedly different from the prior art approach to adaptive signal processing because no noise reference signal is generated and no noise canceller is used by the adaptive signal processor 210. The true signal is determined directly from the given conditions and the mathematically derived relationships shown in the equations above. The adaptive filter 212 can be designed in a well known manner to improve the accuracy and correctness of the true signal. The procedure for the selection of the proper values for the ratio constants α and β is discussed below.

It should be noted that the above discussion relates to the measurement of the true intensity of light transmitted from the Red light source 6. However, those skilled in the art can readily recognize that the same principles apply to the measurement of the true intensity of light transmitted from the IR light source 8. The true intensity signal r*(t) can be directly derived from the true intensity signal R*(t) using the relationship of equation (7). Thus, both true intensity signals R*(t) and r*(t) can be directly derived once the correct values have been determined for the ratio constants α and β.

As stated above, the signal R'(t) provided to the reference input 216 is equation (11) for selected values of the ratio $r_a$.

The system 180 must determine values for α and β so that R'(t)=R*(t), to assure that the filter output 214 will represent the true signal intensity R*(t). It can be shown that the ratio constants α and β are interrelated. If one assumes that the true signal and the noise signal are uncorrelated, and that α≠β, the following equations relate the ratio constants α and β:

$$\alpha = \frac{\int_t R^2(t) - \beta \int_t R(t)r(t)}{\int_t R(t)r(t) - \beta \int_t r^2(t)} \quad (13)$$

$$\beta = \frac{\int_t R^2(t) - \alpha \int_t R(t)r(t)}{\int_t R(t)r(t) - \alpha \int_t r^2(t)} \quad (14)$$

As seen in equations (13) and (14), the ratio constants α and β are symmetric and thus only one value, either α or β, need be determined. The following description provides an example of the determination of the values of the ratio constants α and β.

Figure 9:
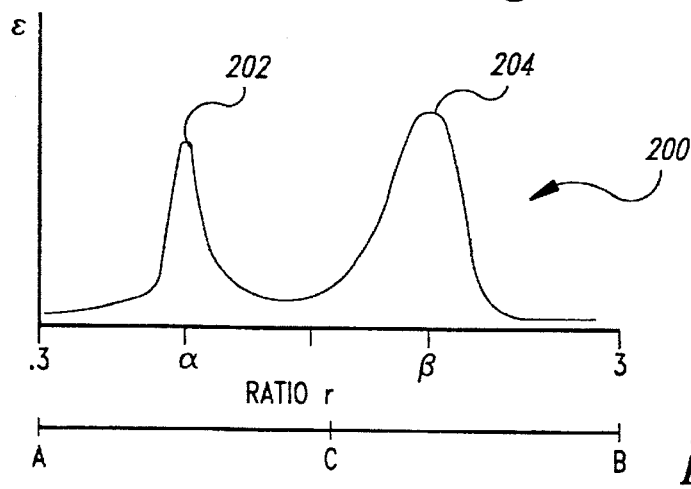
FIG. 9 illustrates a waveform used in the calculation of a reference signal by the analyzer of FIG. 8.

As previously illustrated by equation (9) above, the value of the ratio constants α and β lie between 0.3 and 3.0. The system 180 uses a peak detector 250 to derive the values of the ratio constants α and β without scanning the entire range. This approach provides a great computational advantage over the prior art since far fewer calculations are performed to detect the peak value. With reference to FIG. 9, a waveform 200 has a first peak 202 having a value of the ratio $r_a$ that corresponds to the ratio constant α. In addition to the peak 202, the waveform 200 has a second peak 204 with a value for the ratio $r_a$ that corresponds to the ratio constant β.

The end points of this range are designated as end points A and B, respectively. The peak detector divides the range A–B in half and looks for a peak in one of the two subdivided intervals. If a peak is found in one subdivided interval, the remaining interval is discarded. This process is repeated until a peak is detected. This process is described in detail below.

The peak detector 250 detects one the of peaks 202 and 204 using the technique described below. However, it is not known which peak has been detected. The value for the remaining on the peaks 202 and 204 can be derived mathematically as can the determination of which peak corresponds to the ratio constant α and which peak corresponds to the ratio constant β. The techniques used to detect and identify the peaks 202 and 204 are discussed below. The peak detector 250 provides a corrected reference signal, R'(t), to the filter input 216. Once the ratio constants α and β have accurately been determined, the corrected reference signal R'(t) equals the signal R*(t), the true intensity of the light from the Red light source 8 (see FIG. 4). If the values of the ratio constants α and β are precisely known, the reference signal R'(t) equals the signal R*(t) exactly. In that case, there is no need to perform further digital signal processing using the adaptive signal processor 210. However, if there is some error in the determination of the ratio constants α and β, the adaptive filter 212 can be used to provide a "clean" output signal that more accurately represents the true intensity, R*(t). In the presently preferred embodiment, the true intensity output signals 188 and 190 (see FIG. 7) are taken from the filter output 214 (see FIG. 8) to compensate for such minor errors in the calculation of the ratio constants α and β.

Figure 10:
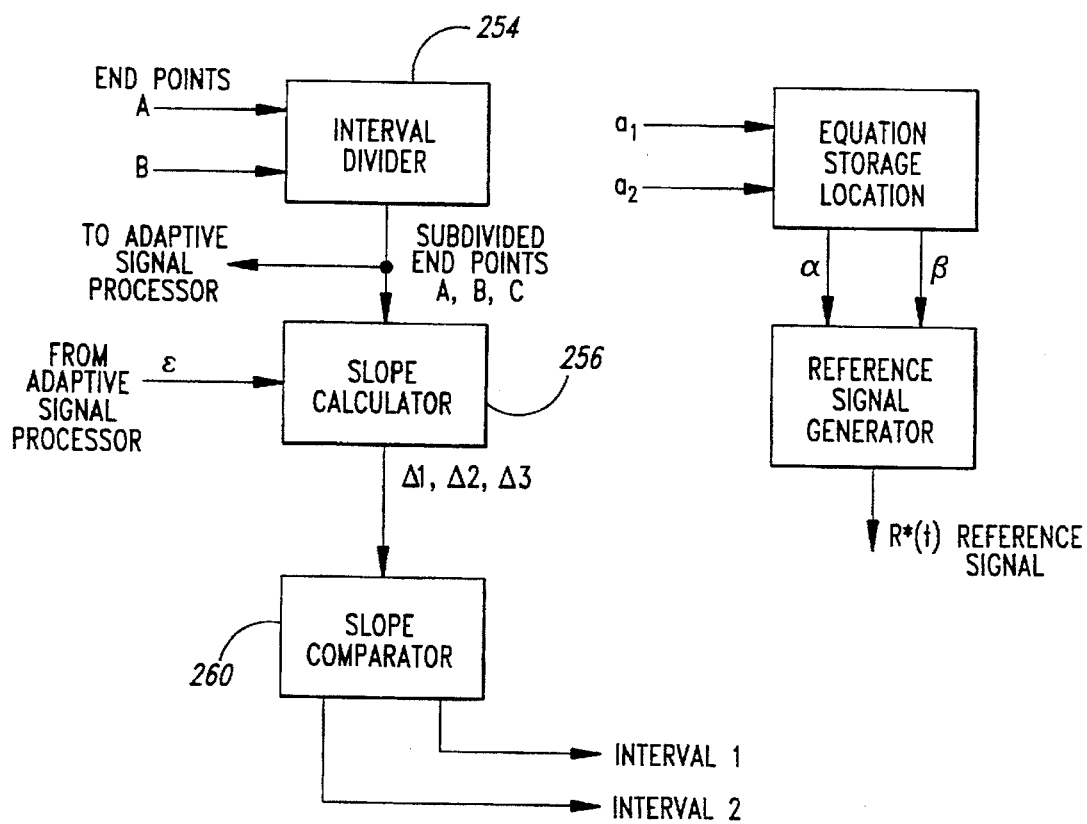
FIG. 10 is a functional block diagram of the peak detector of FIG. 8.

A detailed functional block diagram of the peak detector 250 is shown in FIG. 10. The peak detector 250 includes an interval divider 254 that receives end points A and B and divides the range of possible values for the ratio $r_a$ into two equal intervals, having end points designated in FIG. 9 as A, B, and C, respectively where the first interval has end points A and C and the second interval has end points C and B. The adaptive signal processor 210 (see FIG. 8) calculates the error signal ε for values of the ratio $r_a$ at first and second ends of each of the two intervals. To calculate the error signal ε at endpoint A, the adaptive signal processor 210 substitutes the value of the ratio $r_a$ at the end point A and uses equations (11) and (13) to derive the reference signal R'(t) for that particular value of the ratio $r_a$. For example, the end point A in FIG. 9 has a value of 0.3. The analyzer 182 uses the value of 0.3 for the ratio constant β in equation (13) and solves for the ratio constant α. In turn, those values for the ratio constants α and β are substituted into equation (11) to determine the reference signal R'(t) for ratio $r_a$=0.3. The error signal 232 has a value ε corresponding to the ratio $r_a$ at the end point A. Similarly, the reference signal R'(t) for ratio $r_a$=3.0 is used to determine the value ε for the ratio $r_a$ at the end point B.

A slope calculator 256 calculates slopes at the end of each of the two intervals using the error signal ε calculated for the first and second ends of each of the two intervals. Thus, the slope calculator 256 performs three slope calculations to generate slope values designated herein as $\Delta_1$, $\Delta_2$, and $\Delta_3$. The values $\Delta_1$ and $\Delta_2$ are slope values for the first and second ends of interval one and $\Delta_2$ and $\Delta_3$ are slope values for the first and second ends of interval two. A slope comparator 260 uses the slope values $\Delta_1$, $\Delta_2$, and $\Delta_3$, to search each of the two intervals for a peak. If a peak is found in the first interval, the second interval is discarded and the subdivide process is repeated on the first interval until the peak is found. Conversely, if a peak is found in the second interval, the first interval is discarded and the subdivide process is repeated on the second interval until the peak is found. Thus, with each set of slope measurements, the range of values for the peak is divided in half. This "divide and conquer" approach greatly reduces the number of calculations performed by the pulse oximeter. A reference signal generator 262 generates the reference signal R'(t) by taking the values of the ratio $r_a$ at the end points and using the previously discussed mathematical equations in the mathematical relationship storage area 192 (see FIG. 7). When the precise values for the ratio constants α and β have been determined, the reference signal generator 262 generates the reference signal R'(t) equal to the true intensity R*(t). Details of the divide and conquer technique are provided below in conjunction with the flow chart of FIGS. 11A–11B.

Figure 11A:
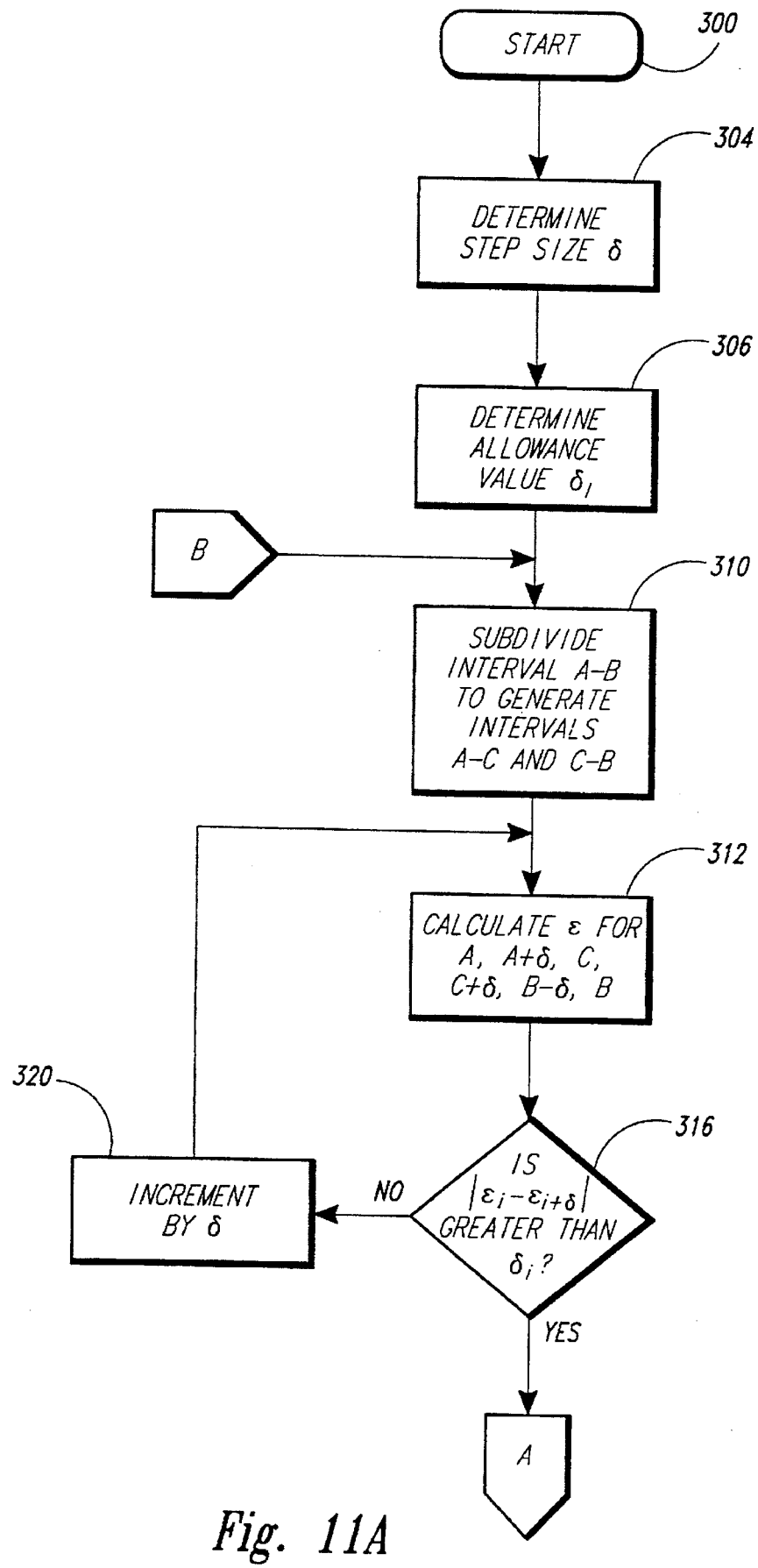
FIGS. 11A and 11B are flowcharts of the operation of the peak detector of the system of FIG. 10.
Figure 11B:
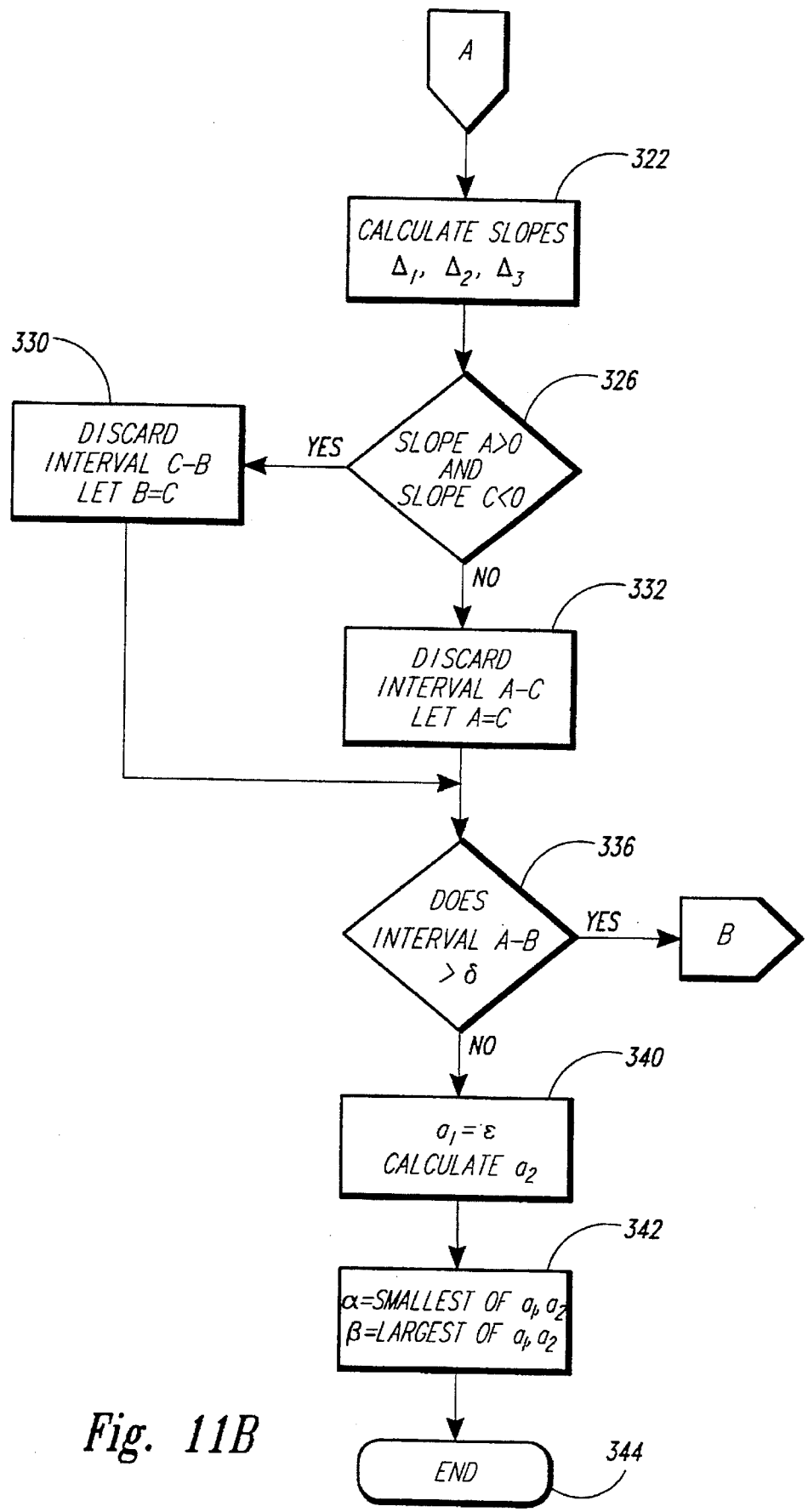

At the start 300, in FIG. 11A, the peak detector 250 (see FIG. 10) is provided with the end points A and B corresponding to the entire range of possible ratios. In step 304, the system determines a step size δ. The interval A–B may be subdivided into a number of steps with the accuracy of peak detection being dependent on the step size. For example, the interval A–B could be divided into 0.1 increments, such that δ=0.1. Thus, the peak will be detected, and the value of the ratio constants α and β determined, within a value of 0.1. It is clear to those of ordinary skill in the art that other step sizes may be chosen. A large step size requires less calculations, but results in a less accurate determination of the peak value. Conversely, a small value for δ results in a more accurate determination of the peak, but at the cost of an increased number of calculations. In the presently preferred embodiment, the step size, δ, is selected to be 0.1.

In step 306, the system 180 determines an allowance value $\delta_1$. The allowance value $\delta_1$ specifies a minimum change in the amplitude of the value $\epsilon$ of the error signal 232 (see FIG. 8) that will be used to determine the slope. This assures that small perturbations in the waveform 200 will not be interpreted as peaks by the peak detector 250.

In step 310, the peak detector 250 (see FIG. 10) calculates a point C substantially halfway between the points A and B thus subdividing the interval A–B to generate two substantially equal intervals A–C and C–B. The adaptive signal processor 210 (see FIG. 8) calculates the error signal value $\epsilon$ for the points A, A+$\delta$, C, C+$\delta$, B–$\delta$, and B. Thus, the adaptive signal processor calculates the error signal value $\epsilon$ for six values of the ratio $r_a$. As previously described, the value of the ratio $r_a$ at each of these six points is substituted for $\alpha$ in equation (14) to find a value for $\beta$. The resultant values for $\alpha$ and $\beta$ are substituted into equation (11) to calculate the reference signal R'(t) for each of the six values of the ratio $r_a$.

In decision 316, the peak detector determines whether the slope at points A and A+$\delta$, C and C+$\delta$, and B–$\delta$ and B are greater than the allowance value $\delta_1$. In the presently preferred embodiment, the peak detector 250 determines whether the slope at point A and point A+$\delta$ is sufficient by comparing the absolute value of $\epsilon$ at point A minus the value of $\epsilon$ at point A+$\delta$ with the allowance value $\delta_1$. If the absolute value is not greater than $\delta_1$, this indicates that there is not change to make the slope calculation reliable. In that case, the peak detector 250 increments by the value $\delta$ in step 320 and returns to step 312 to repeat the process until the absolute value is greater than $\delta_1$. The peak detector 250 performs similar calculations on points C and C+$\delta$, and B–$\delta$ and B. It should be noted that, in the presently preferred embodiment, the peak detector 250 performs this calculation independently at each of the end points. That is, if the slope at the end point A is determined by point A and A+2$\delta$, the peak detector 250 does not automatically increment points C and B to have a 2$\delta$ slope measurement.

Because of the nature of the curve in FIG. 9, the slope at point A is typically greater than 0, while the slope at point B is typically less than 0. The peak detector 250 assumes that the slope at end point A is positive, while the slope at end point B is negative. The process described above for the allowance value $\delta_1$ assures that the slope at points A and B are as expected. When the absolute value at each of the end points is greater than $\delta_1$, the result of decision 316 is YES. In that event, the peak detector 250, in step 322, shown in FIG. 11B, calculates the slopes $\Delta_1$, $\Delta_2$, and $\Delta_3$ in a conventional manner.

The slope comparator 260 compares the slopes at the points A, B, and C to determine whether a peak is contained in a first interval, A–C, or in the second interval C–B. If the interval A–C contains a peak, the slope at end point C will be negative. Conversely, if a peak is present in interval 2, the slope at point C will be positive. In decision 326, the slope comparator 260 determines whether the slope at end point C is negative. If the slope at end point C is negative, it means that the slope changed from a positive value at endpoint A to a negative value at endpoint C thus indicating that a peak is contained somewhere within the interval A–C. In that event, the result of decision 326 is YES and, in step 330, the peak detector 250 discards the interval C–B and redefines the end point B as having value C. Thus, there is a new interval A–B that corresponds to the previous interval A–C.

If the slope at point C is positive and the slope at point B is negative, it means that the slope changed from a positive value at endpoint C to a negative value at endpoint B thus indicating that a peak is contained somewhere within the interval C–B. In that event, the result of decision 326 is NO, and the peak detector 250 discards the interval A–C in step 332. The peak detector 250 also resets the end point A to have the value C. Thus, the new interval A–B is defined by the previous end points C and B.

In decision 336, the peak detector 250 determines whether the new interval A–B is greater than $\delta$. If the new interval A–B is less than $\delta$, it indicates that the peak detector 250 has determined the value of the peak to within the tolerance specified by the step size $\delta$ in step 304 (see FIG. 11A). If the new interval A–B is greater than $\delta$, the result of decision 336 is YES, and the system returns to step 310 in FIG. 11A to subdivide the interval to again generate intervals A–C and C–B. In this manner, the peak detector 250 continually subdivides the interval in half and determines in which half the peak is located. This peak calculation requires substantially fewer calculations than the prior art system of scanning the entire range from 0.3 to 3.0 for the ratio $r_a$.

When the peak detector 250 has subdivided the intervals such that the interval A–B is not greater than $\delta$, the result of decision 336 is NO. At that point, the peak has been located to within the tolerance specified by the step size $\delta$ in step 304.

At this point, a peak has been detected, but the system 180 does not yet know if the detected peak corresponds to $\alpha$ or $\beta$. The peak detector 250, in step 340, designates the error value $\epsilon$ corresponding to the detected peak as $a_1$. This value is substituted as $\beta$ in equation (13) above, to calculate a value $a_2$. It should be noted that because of the symmetry of equations (13) and (14), the value $a_1$ could have been substituted as $\alpha$ in equation (14). In either case, solving equation (13) or (14) results in a value designated herein as $a_2$. Based on the constraint of equation (9), wherein $\alpha$ is less than $\beta$, the peak detector 250, in step 342, designates the smaller of the values $a_1$ and $a_2$ as $\alpha$. The larger of the values $a_1$ and $a_2$ is designated as $\beta$. The peak detector 250 ends its calculation in step 344 with values of $\alpha$ and $\beta$ having been determined.

Following the calculation of $\alpha$ and $\beta$ by the peak detector 250, the values for $\alpha$ and $\beta$ may be substituted into equation (11) above to accurately determine the reference R'(t) equal to the true intensity R*(t). The newly calculated value for R*(t) is provided to the reference input 216 (see FIG. 8) of the adaptive filter 212. Following the calculation of an accurate reference signal based on correct values for the ratio constants $\alpha$ and $\beta$, the filter output 214 is the true intensity R*(t). It should be noted that a the true intensity of r*(t) of light transmitted from the IR light source 8 can be calculated using equation (7) above.

The analyzer 182 (see FIG. 7) produces the ratio output 192, and the value for oxygen saturation $S_pO_2$ may be determined in a conventional manner. The optional peak detector 194 may be used to determine peak $S_pO_2$ levels. Thus, the analyzer 182 (see FIG. 7) directly produces reference signals equal to the true intensities. In practice, these true intensity signals are derived from the filter output 214. This direct calculation of the true intensities is performed without having to generate a noise reference signal as is done in the prior art, and without having to use digital signal processing correlation cancellation techniques that require a significant number of computational steps. Furthermore, the analyzer 182 requires significantly fewer calculations to determine accurate values for the ratio constants $\alpha$ and $\beta$.

The technique described above assumes that both the true signal and the noise signal are present in the measured signal, as indicated by equations (4)–(5). That is, the measured signal R(t) contains the noise signal N(t) as well as the true intensity R*(t). The technique described above will not accurately detect the values for the ratio constants α and β if only one signal, either the true intensity or the noise signal, is present in the measured signal. This condition can be detected by computing a correlation factor. The correlation factor is defined as:

$$cf = \frac{\int_t r(t)R(t)}{\sqrt{\int_t r^2(t) \cdot \int_t R^2(t)}} \times 100\% \quad (15)$$

for any given time interval. The absolute value of the correlation factor is less than or equal to 100%. The correlation factor indicates how well correlated the two measured signals R(t) and r(t) with each other. A larger value for the correlation factor indicates a greater degree of correlation between the measured signals, and a smaller correlation factor value indicates less correlation between the measured signals. When R(t) and r(t) are completely correlated, then R(t) equals αr(t), and the correlation factor equals 100%. It is known that under this condition, the measured signals are either all true signals or all noise signals, but not a mixture, assuming that the true signal and the noise are uncorrelated. When the correlation factor equals 100%, the technique described above cannot be applied. However, it is a rare occurrence that there is no noise present in the measured signal. Furthermore, it is possible to determine whether the measured signal is solely the true intensity, or solely a noise signal. A noise signal can be discarded, while the true intensity signal may be used to calculate the oxygen saturation in a conventional manner.

Figure 12:
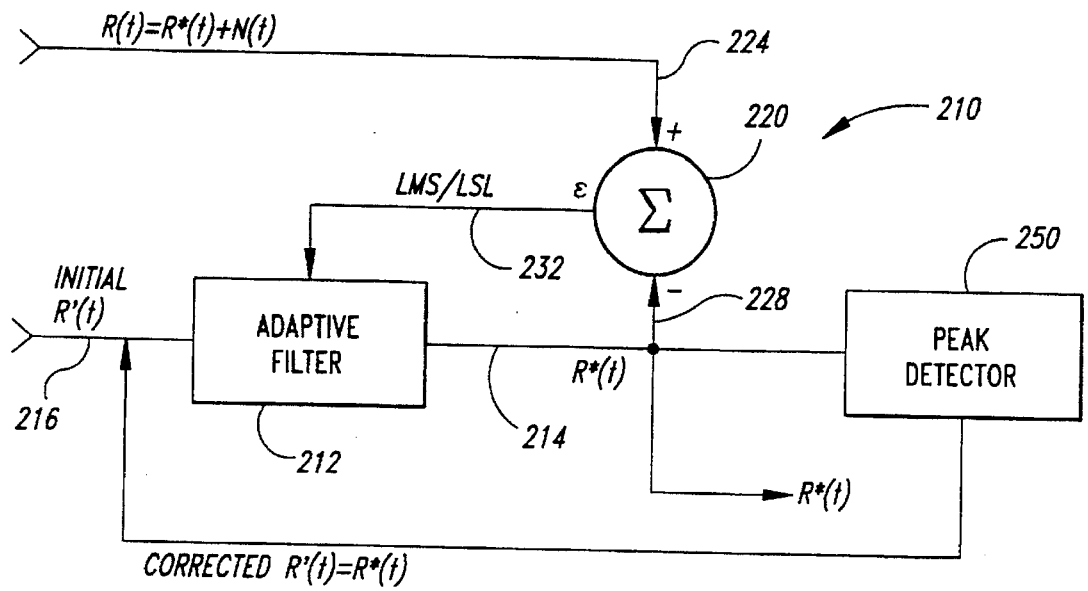
FIG. 12 is a functional block diagram of an alternative embodiment of the analyzer of FIG. 7.

The embodiment of the analyzer 128 illustrated in FIG. 8 uses the error output signal 232 to determine the values for the ratio constants α and β. An alternative embodiment of the analyzer 128 is illustrated in FIG. 12. The analyzer 128 also uses an adaptive signal processor 210, similar to that shown in FIG. 8. However, the input to the peak detector 250 is not taken from the error output 232, but rather directly from the filter output 214 of the adapter filter 212. The relationship between the filter output 214 and the ratio constants α and β is illustrated by the following equations:

$$A(R''(r_a)) = E(R''^2(t, r_a)) = \int_t (R^*(t))^2 \, dt, \; r_a = \alpha \quad (16)$$

$$A(R''(r_a)) = E(R''^2(t, r_a)) = \int_t (N(t))^2 \, dt, \; r_a = \beta \quad (17)$$

where $A(R''(r_a))$ is the amplitude of the filter output 214, and $E(R''^2(t, r_a))$ is the expectation value of the squared signal $R''^2(t, r_a)$. Those skilled in the art will recognize that equations (16) and (17) are measures of the output power from the filter output 214.

Equations (16) and (17) above indicate that the amplitude of the filter output 214 has maximum values when the ratio $r_a$ has values equal to α and β. The peak detection process previously described is used to determine the correct values for the ratio constants α and β. That is, various values for the ratio $r_a$ at the endpoints A, B, and C are substituted into equations (14) and (11) to generate the reference signal R'(t) for selected values of the ratio $r_a$. The filter output 214 will have the same shape as the waveform 200 (see FIG. 9) for values of the ratio $r_a$ ranging from 0.3 to 3.0. The peak detector 250 operates in the manner previously described to detect peaks, however, the detected peaks are from the filter output 216 rather than the error signal 232 as was the case in the embodiment of FIG. 8. When correct values for the ratio constants α and β have been determined, these values are substituted into equation (11) to calculate the correct reference signal for the filter input 216. Following the determination of the appropriate reference signal, the reference signal R'(t) equals the true intensity R*(t). As discussed above, the filter output 214 is used to provide the true intensity outputs 188 and 190 to minimize the effect of errors in the calculation of the ratio constants α and β. As previously discussed, the true intensity r*(t) of light transmitted by the IR light source 8 can be easily calculated using equation (7). The alternative embodiment of FIG. 12 is significantly different from the systems known in the prior art because no noise reference signal is derived from the measured signals. Rather, the true intensity outputs 188 and 190 are directly derived using the ratio constants α and β and the mathematical relationships discussed above. Furthermore, the embodiment illustrated in FIG. 12 does not use the error output 232 to detect peak values and to determine the values for the ratio constants α and β.

Figure 13:
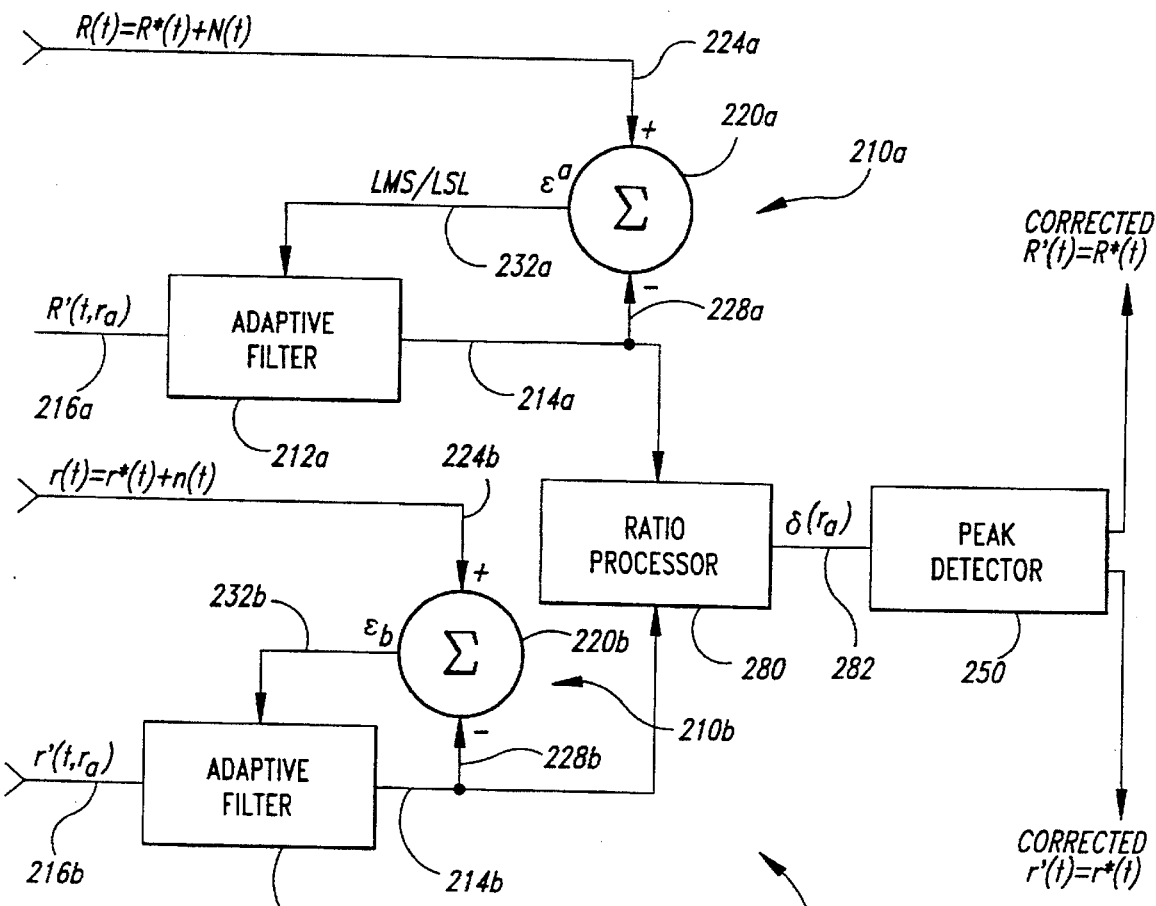
FIG. 13 is a functional block diagram of another alternative embodiment of the analyzer of FIG. 7.

A third embodiment of the analyzer 128 is illustrated in FIG. 13. The embodiment of FIG. 13 utilizes first and second adaptive signal processors 210, which are designated herein as 210a and 210b, respectively. The adaptive signal processors 210a and 210b are constructed in the same manner as the adaptive signal processor of FIG. 12. However, the filter outputs 214a and 214b are coupled to a ratio processor 280 rather than to the peak detector 250 (see FIG. 12). The adaptive signal processor 210a receives the measured signal R(t) (i.e., R*(t)+N(t)) as an input 224a to the subtractor 220a, as previously described. The filter input 216a is provided with signal R'(t), derived from equation (11), as an approximation of the true intensity R*(t). The reference signal R'(t) is derived in the manner described above using equations (11)–(14), for values of the ratio $r_a$ corresponding to endpoints A, B, and C of the range of possible values of the ratio $r_a$. Once the correct values for the ratio constants are selected, the reference signal R'(t) equals the true intensity R*(t).

Similarly, adaptive signal processor 210b receives the measured signal r(t) (i.e., r*(t)+n(t)) as an input 224b to the subtractor 220b, as previously described. The reference signal r'(t) can be derived directly from the reference signal R'(t) using equation (7). When the correct values for the ratio constants α and β are selected, the reference signal r'(t)=r*(t).

The filter output 214a from the adapter signal processor 210a and the filter output 214b from the adapter signal processor 210b are provided to the ratio processor 280. The ratio processor 280 determines a ratio between the two filter outputs 214a and 214b, and generates an output 282 indicative of the ratio between the two filter outputs.

As shown below in equation (18), the output 282 of the ratio processor 280 has the following form:

$$Q(r_a) = \frac{\int_t R''(t, r_a) \times r''(t, r_a)}{\int_t r''(t, r_a) \times r''(t, r_a)} \; ; \text{ and} \quad (18)$$

$$\delta(r_a) = (Q(r_a) - r_a)^2$$

where the ratio $r_a$ has a value ranging from 0.3 to 3.0, the physiological range of values previously discussed. When $r_a$ equals α, equation (18) reduces to the following:

$$Q(\alpha) = \frac{\int_t R''(t, \alpha) x r''(t, \alpha)}{\int_t r''(t, \alpha) x r''(t, \alpha)} \; ; \text{and}$$

$$\delta(\alpha) = (Q(\alpha) - \alpha)^2 \equiv 0.$$

Similarly, it can be shown that $\delta(\beta) = (Q(\beta) - \beta)^2 \approx 0$. Thus, the output 282 of the ratio processor 280 is approximately zero at points where the ratio $r_a = \alpha$ and $\beta$. At other values for $r_a$, the output 282 of the ratio processor 280 is large. A variation of the peak detector 250 can be used to detect the minimum values that correspond to $\alpha$ and $\beta$, respectively. The adaptation of the peak detector 250 to determine minimum values is well known in the art, and need not be described herein.

The various embodiments of the analyzer 128 discussed with respect to FIGS. 7, 11, and 12, all provide different techniques for determining accurate values for the ratio constants $\alpha$ and $\beta$. Once these ratio constants $\alpha$ and $\beta$ have been accurately determined, the true intensity outputs 188 and 190 can be directly derived. The true intensity signals can be applied as the reference input 216 to the adaptive filter 212 in each embodiment to provide additional signal enhancement. Once the reference signal has been applied to the adaptive filter 212, the output 214 of the adaptive filter is a motion artifact free signal $R^*(t)$ and $r^*(t)$. The accurate pulse oximeter readings, such as $S_pO_2$, peak $S_pO_2$, and plethysmography can be derived by conventional techniques using the clean signals provided by the present invention.

In operation, many of the components described above may be incorporated into a digital signal processor and/or a digital computer. The programming details of the digital signal processor and computer are well known to those of ordinary skill in the art and need not be discussed herein.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. A system for the enhancement of physiological signals for the measurement of blood oxygen in a subject, the system comprising:

first and second light sources to direct light toward the subject, said first and second light sources producing first and second light signals of first and second wavelengths, respectively;

a light detector positioned to detect said first and second light signals after interaction with the subject and to generate first and second signals indicative of an intensity of said first and second detected light signals, respectively, said first generated signal having a first portion arising from light transmitted from said first source and a second portion arising from a first interference light source, said second generated signal having a first portion arising from light transmitted from said second source and a second portion arising from a second interference light source;

an adaptive signal processor having a signal input coupled to said light detector to receive said first generated signal, an adaptive filter having an input to receive a reference signal, and an output, and an error output to generate an error signal, wherein said error output is coupled to said adaptive filter to adjust said adaptive filter so that said error signal has a minimum value;

a storage location containing a mathematical relationship of said first and second portions of said first and second generated signals and a first ratio constant;

a reference signal generator to generate said reference signal based on an estimated value of said first ratio constant; and a peak detector to receive an output signal from said adaptive signal processor and determine a calculated value for said first ratio constant corresponding to a first peak value of said output signal over a predetermined range of possible ratios, said reference signal generator generating said first portion of said first detected signal and said first portion of said second detected signal based on said mathematical relationship and said calculated value of said first ratio constant.

2. The system of claim 1 wherein said peak detector includes means for subdividing said predetermined range into first and second substantially equal ranges to determine a peak location in either said first or second ranges, said peak detector continuing to subdivide one of said first or second ranges containing said peak until said peak detector determines said calculated value of said first ratio constant corresponding to said first peak value.

3. The system of claim 1 wherein said output signal received by said peak detector is selected from a set of output signals comprising said error signal output and said adaptive filter output.

4. The system of claim 1, further including an oxygen saturation calculating circuit to determine blood oxygen saturation of the subject based on said calculated value of said first ratio constant.

5. The system of claim 1, further including a data table interrelating said calculated value of said first ratio constant with blood oxygen saturation level.

6. The system of claim 1 wherein said calculated value of said first ratio constant is a time-varying signal, the system further including a peak saturation calculating circuit to calculate a peak oxygen saturation level from said time-varying signal.

7. The system of claim 1 wherein said first and second wavelengths are in the red and near-infrared wavelength range, respectively.

8. The system of claim 1 wherein said mathematical relationship has the following form:

$$R^*(t) = \frac{\alpha R(t) - \alpha \beta r(t)}{\alpha - \beta}$$

where $R^*(t)$ corresponds to said first portion of said first generated signal, $R(t)$ corresponds to said first generated signal, including said first and second portions of said first generated signal, $r(t)$ corresponds to said second generated signal, including said first and second portions of said second generated signal, $\alpha$ is said first ratio constant and corresponds to a ratio of said first portion of said first generated signal to said first portion of said second generated signal, and $\beta$ is a second ratio constant and corresponds to a ratio of said second portion of said first generated signal to said second portion of said second generated signal.

9. The system of claim 1 wherein said mathematical relationship has the following form:

$$r^*(t) = \frac{R(t) - \beta r(t)}{\alpha - \beta}$$

where $r^*(t)$ corresponds to said first portion of said second generated signal, $R(t)$ corresponds to said first generated signal, including said first and second portions of said first generated signal, r(t) corresponds to said second generated signal, including said first and second portions of said second generated signal, α is said first ratio constant and corresponds to a ratio of said first portion of said first generated signal to said first portion of said second generated signal, and β is a second ratio constant and corresponds to a ratio of said second portion of said first generated signal to said second portion of said second generated signal.

10. A method for the enhancement of physiological signals for the measurement of blood oxygen in a subject, the method comprising the steps of:

directing light from first and second light sources of different wavelengths toward the subject;

detecting signals from said first and second light sources after interaction with the subject and generating first and second signals corresponding to an intensity of said first and second detected signals, respectively, said first generated signal having a first portion arising from light transmitted from said first source and a second portion arising from a first interference light source, said second generated signal having a first portion arising from light transmitted from said second source and a second portion arising from a second interference light source;

coupling said first generated signal to a signal input of an adaptive signal processor having an adaptive filter having an input to receive a reference signal, and an output, and an error output generating an error signal wherein said error signal is coupled to said adaptive filter to adjust said adaptive filter so that said error signal has a minimum value;

coupling an output signal from said adaptive signal processor to a peak detector and calculating a first ratio value corresponding to a first detected peak value of said error signal over a predetermined range of possible ratio values;

generating a first reference signal based on a mathematical relationship of said first and second portions of said first and second generated signals, and said first ratio value; and coupling said first reference signal to said adaptive filter input wherein said filter output generates said first portion of said first generated signal.

11. The method of claim 10 wherein said output signal from said adaptive signal processor is said error signal and said calculated first ratio value is based on said first detected peak value in said error signal.

12. The method of claim 10 wherein said output signal from said adaptive signal processor is derived from said adaptive filter output and said calculated first ratio value is based on said first detected peak value in said output signal derived from adaptive filter output.

13. The method of claim 10 wherein said peak detector performs the steps of subdividing said predetermined range into first and second substantially equal ranges and detecting said first peak value in either said first or second ranges, said peak detector continuing to subdivide one of said first or second ranges containing said first detected peak value until said peak detector detects said first peak value within a predetermined threshold.

14. The method of claim 12, further including the step of generating said first portion of said second generated signal based on said mathematical relationship and said calculated first ratio value.

15. The method of claim 14 wherein said first ratio value is a ratio of said first portion of said first generated signal to said first portion of said second generated signal.

16. The method of claim 15 wherein said calculated first ratio value is a time-varying signal, the method further including the step of calculating a peak oxygen saturation level from said time-varying signal.

17. The method of claim 10, further including the step of determining a blood oxygen saturation level of the subject based on said calculated first ratio value.

18. The method of claim 10, further including the step of determining a blood oxygen saturation level of the subject using a data table interrelating said calculated first ratio value with blood oxygen saturation level.

19. The method of claim 10 wherein said mathematical relationship has the following form:

$$R^*(t) = \frac{\alpha R(t) - \alpha\beta r(t)}{\alpha - \beta}$$

where $R^*(t)$ corresponds to said first portion of said first generated signal, $R(t)$ corresponds to said first generated signal, including said first and second portions of said first generated signal, $r(t)$ corresponds to said second generated signal, including said first and second portions of said second generated signal, α is said first ratio constant and corresponds to a ratio of said first portion of said first generated signal to said first portion of said second generated signal, and β is a second ratio constant and corresponds to a ratio of said second portion of said first generated signal to said second portion of said second generated signal.

20. The method of claim 10 wherein said mathematical relationship has the following form:

$$r^*(t) = \frac{R(t) - \beta r(t)}{\alpha - \beta}$$

where $r^*(t)$ corresponds to said first portion of said second generated signal, $R(t)$ corresponds to said first generated signal, including said first and second portions of said first generated signal, $r(t)$ corresponds to said second generated signal, including said first and second portions of said second generated signal, α is said first ratio constant and corresponds to a ratio of said first portion of said first generated signal to said first portion of said second generated signal, and β is a second ratio constant and corresponds to a ratio of said second portion of said first generated signal to said second portion of said second generated signal.

* * * * *

Adverse Decision in Interference

Patent No. 5,662,105, Jonathan Tien, SYSTEM AND METHOD FOR THE EXTRACTMENT OF PHYSIOLOGICAL SIGNALS, Interference No. 105,472, final judgment adverse to the patentees rendered November 24, 2006, as to claims 1-20.

(*Official Gazette* June 12, 2007)